United States Patent
Drouot et al.

(10) Patent No.: US 8,481,515 B2
(45) Date of Patent: Jul. 9, 2013

(54) DERIVATIVES OF CHOLEST-4-EN-3-ONE OXIME, PHARMACEUTICAL COMPOSITIONS CONTAINING THEM AND PREPARATION METHOD

(75) Inventors: Cyrille Drouot, Draguignan (FR); Delphine Maux, Biot (FR)

(73) Assignee: Trophos, Marseille (FR)

( * ) Notice: Subject to any disclaimer, the term of this patent is extended or adjusted under 35 U.S.C. 154(b) by 728 days.

(21) Appl. No.: 12/158,640

(22) PCT Filed: Dec. 15, 2006

(86) PCT No.: PCT/FR2006/002740
§ 371 (c)(1),
(2), (4) Date: Mar. 2, 2009

(87) PCT Pub. No.: WO2007/080270
PCT Pub. Date: Jul. 19, 2007

(65) Prior Publication Data
US 2009/0203662 A1    Aug. 13, 2009

(30) Foreign Application Priority Data
Dec. 20, 2005    (FR) ...................................... 05 12947

(51) Int. Cl.
*A61K 31/575*    (2006.01)
*C07J 41/00*    (2006.01)

(52) U.S. Cl.
USPC ............................ 514/169; 514/177; 552/520

(58) Field of Classification Search
USPC ................... 552/520; 514/177, 169
See application file for complete search history.

(56) References Cited

U.S. PATENT DOCUMENTS
7,858,603 B2 * 12/2010 Bordet et al. ................ 514/169

FOREIGN PATENT DOCUMENTS
WO    WO 2004/082581    * 9/2004

OTHER PUBLICATIONS

Bordet et al., Identification and Characterization of Cholest-4-en-3-one, Oxime (TRO19622), A Novel Drug Candidate for Amyotrophic Lateral Sclerosis, Journal of Pharmacology and Experimental Therapeutics, 322 (2):709-720 (2007).

Mattson et al., Modification of brain aging and neurodegenerative disorders by genes, diet, and behavior, Physiol. Rev., 82:637-672 (2002).

* cited by examiner

*Primary Examiner* — Sabiha Qazi
(74) *Attorney, Agent, or Firm* — Browdy and Neimark, PLLC

(57) ABSTRACT

The object of the invention is the use as a drug of a compound fitting formula I

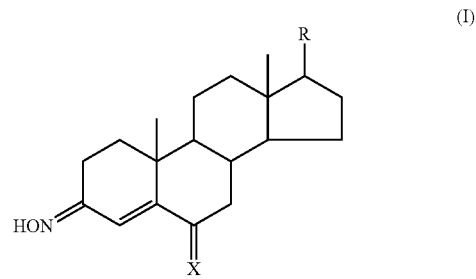

wherein X represents an oxygen atom or a =N—OH group and R represents a group selected from

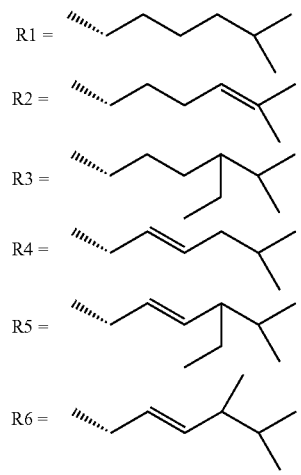

or one of its esters and/or of its addition salts with pharmaceutically acceptable acids, particularly as a cytoprotective drug, preferentially a cardioprotective and/or neuroprotective drug, the compounds of formula I wherein R is R2, R3, R4, R5 or R6 as novel compounds as well as their preparation method and use.

1 Claim, No Drawings

DERIVATIVES OF CHOLEST-4-EN-3-ONE OXIME, PHARMACEUTICAL COMPOSITIONS CONTAINING THEM AND PREPARATION METHOD

The present invention relates to the use of derivatives of cholest-4-en-3-one oxime as drugs, notably as cytoprotective drugs, particularly as neuroprotective or cardioprotective drugs. Said drugs are particularly suitable for pathologies and traumas related to cell degeneration or death, particularly those of motoneurons, and/or cardiac cells. The invention also relates to pharmaceutical compositions containing said compounds, to novel derivatives and to their preparation method.

Cell degenerative processes are characterized by dysfunction of the cells often causing undesirable cell activities and cell death.

Cells have developed adaptation mechanisms, in response to stress, which extend their life time, or delay or even prevent cell death (cytoprotective mechanisms).

However, these cytoprotective mechanisms are often insufficient, inadequate, or induced too late in order to be effective and the cells die. It may therefore prove to be of interest to have novel cytoprotective drugs which would promote cytoprotection. This is one of the objects of the present invention.

Among the main mechanisms of cell death, a distinction is essentially made between necrosis, apoptosis, and necroptosis.

Necrosis is a so-called "accidental" cell death which occurs during damage to tissue. It is the plasmic membrane of the cell which is affected the most, causing modification of homeostasis of the cell. The cells will soak up water to the extent that this will cause lysis of their plasmic membrane. This cell lysis leads to releasing the cytoplasm contents into the surrounding medium. Necrosis is at the origin of the inflammatory process.

Necrosis may affect a set of cells or a tissue while other neighboring portions remain alive. The resulting transformation is mortification of the cells or of the tissues.

In other words, necrosis is defined by morphological modifications which occur when a cell reaches the end of its life as a result of events such as a significant trauma such as interruption or reduction of the blood supply at an organ, hyperthermia (significant rise in temperature), intoxication by a chemical, a physical shock, etc. . . .

One of the most known necroses is that of the myocardium infarction (interruption of the blood stream supply at the cardiac muscle) due to occlusion (obstruction) of a coronary artery.

Apoptosis is an integral part of the normal physiology of an organism. It is a highly regulated physiological form of cell death and it is required for the survival of multicellular organisms. Apoptosis is a process which plays a primordial role during embryogenesis.

Cells in apoptosis or apoptotic cells will isolate themselves from the other cells. Apoptosis usually involves individual cells in a tissue and does not cause inflammation. One of the characteristic morphological points of apoptosis is the significant condensation of both the nucleus and the cytoplasm which induces significant reduction in the cell volume. The nucleus then fragments, each fragment is surrounded by a dual envelope. Apoptotic bodies (cytoplasmic and nuclear elements) are then released and will be absorbed through phagocytosis by neighboring cells.

Apoptosis may be induced in different ways. For instance, radiation, the presence of a chemical or hormone, are stimuli which may induce a cascade of apoptotic events in the cell. Intracellular signals such as incomplete mitosis or DNA damage may also induce apoptosis.

Apoptosis also occurs after the action of a genotoxic agent or during a disease. Certain pathologies are characterized by abnormal apoptosis, causing the loss of certain cell populations, as for example hepatotoxicity, retinopathies, cardiotoxicity.

A distinction is therefore made between physiological apoptosis and pathological apoptosis. The invention is essentially focused on pathological apoptosis.

There exist other mechanisms of cell death, such as for example necroptosis, which has characteristics of necrosis and apoptosis. A cell which is dying by necroptosis has similar characteristics to those of a cell dying by necrosis, but the biochemical steps of this mechanism are more similar to those of apoptosis. This mechanism of cell death for example occurs in ischemia.

Accordingly, one of the objects of the present invention is to make novel drugs available with which it will be possible to prevent and/or treat necrosis and/or pathological apoptosis and/or necroptosis (anti-necrotic and/or anti-apoptotic and/or anti-necroptotic drugs).

Cell degenerative processes may result inter alia from pathological situations grouped under the term of degenerative diseases or affections, traumas or of exposure to various factors.

These traumas and factors may for example include exposure to radiations (UV, gamma radiations), hypoxia or lack of oxygen, lack of nutrients, lack of growth factors, poisons, cell toxins, waste, environmental toxins, free radicals, reactive oxygens or even to certain medical events and/or procedures such as for example surgical traumas including transplantations. Chemical or biological agents may also be mentioned, used as therapeutic agents within the context of medical treatments such as for example cytostatic agents or anti-inflammatory agents.

Among the most significant pathological situations characterized by a degenerative process, are found:

diseases of the bones, joints, connective tissue and of cartilage, such as osteoporosis, osteomyelitis, arthritises including for example osteoarthritis, rheumatoid arthritis and psoriatic arthritis, avascular necrosis, progressive fibrodysplasia ossificans, rickets, Cushing's syndrome;

muscular diseases such as muscular dystrophy, such as for example Duchenne's muscular dystrophy, myotonic dystrophies, myopathies and myasthenias;

diseases of the skin, such as dermatitises, eczema, psoriasis, aging or even alterations of scarring;

cardiovascular diseases such as cardiac and/or vascular ischemia, myocardium infarction, ischemic cardiopathy, chronic or acute congestive heart failure, cardiac dysrythmia, atrial fibrillation, ventricular fibrillation, paroxystic tachycardia, congestive heart failure, anoxia, hypoxia, secondary effects due to therapies with anticancer agents;

circulatory diseases such as atherosclerosis, arterial scleroses, peripheral vascular diseases, cerebrovascular strokes, aneurisms;

haematological and vascular diseases such as: anemia, vascular amyloidosis, haemorrhages, drepanocytosis, red cell fragmentation syndrome, neutropenia, leukopenia, medullar aplasia, pantocytopenia, thrombocytopenia, haemophilia;

lung diseases including pneumonia, asthma; obstructive chronic disease of the lungs such as for example chronic bronchitises and emphysema;

diseases of the gastrointestinal tract, such as ulcers;

diseases of the liver including viral hepatitises and cirrhoses, diseases of the liver due to toxins and to drugs;

diseases of the pancreas such as for example acute or chronic pancreatitises;

metabolic diseases such as diabetes mellitus and insipid diabetes, thyroiditises;

diseases of the kidneys such as for example acute renal disorders or glomerulonephritis;

viral and bacterial infections such as septicemia;

severe intoxications by chemicals, toxins or medications;

degenerative affections associated with the Acquired Immune Deficiency Syndrome (AIDS);

disorders associated with aging such as the accelerated aging syndrome;

inflammatory diseases such as Crohn's disease, rheumatoid polyarthritis;

auto-immune diseases such as erythematous lupus;

dental disorders such as those resulting in degradation of the tissues such as for example periodontitises;

ophthalmic diseases or disorders including diabetic retinopathies, glaucoma, macular degenerations, retinal degeneration, retinitis pigmentosa, retinal holes or tears, retinal detachment, retinal ischemia, acute retinopathies associated with trauma, inflammatory degenerations, post-surgical complications, medicinal retinopathies, cataract;

disorders of the auditory tracts, such as otosclerosis and deafness induced by some antibiotics;

diseases associated with mitochondria (mitochondrial pathologies), such as Friedrich's ataxia, congenital muscular dystrophy with structural mitochondrial abnormality, certain myopathies (MELAS syndrome, MERFF syndrome, Pearson's syndrome), MIDD syndrome (mitochondrial diabetes and deafness), Wolfram's syndrome, dystonia.

Moreover, neurodegenerative processes are characterized by dysfunction and death of neurons causing the loss of neurological functions mediated by the brain (central nervous system, CNS), the spinal cord and the peripheral nervous system (PNS). They may result i.a. from pathological situations grouped under the term of neurodegenerative diseases or affections, trauma, or exposure to toxins.

The most important pathologies which are characterized by a neurodegenerative process are:

hereditary or sporadic neurodegenerative chronic diseases, notably Alzheimer's disease, Huntington's disease, Parkinson's disease, amyotrophic lateral sclerosis, spinal amyotrophies, Creutzfeldt-Jakob's disease, disseminated sclerosis, amyotrophic lateral scleroses, adrenoleukodystrophy, epilepsy, dementias, schizophrenia, and neurological syndromes associated with AIDS;

neuronal lesions related to aging;

hereditary or lesional peripheral neuropathies, such as Fabry's, Charcot-Marie-Tooth's, Krabbe's diseases, leukodystrophies, diabetic neuropathies and those induced by anti-cancer treatments;

traumas of the brain, of the peripheral nerves or of the spinal cord;

ischemias of the brain or the spinal cord as a result of a cerebrovascular stroke, or induced by lack of blood irrigation;

hereditary, lesional or aging-related degenerations of sensorial neurons of vision, such as macular degenerations, retinitis pigmentosa or degenerations of the optical nerve induced by glaucomas;

hereditary, traumatic or aging-related degenerations of sensorial neurons of hearing causing reduction or loss of audition.

A portion of the signalization routes affected in these pathologies are common to a large number of neurodegenerative diseases. Alzheimer's disease is the most frequent dementia. It causes the appearance of an atrophy of the brain, a predominant loss of neurons in the horn of Ammon and it also affects cholinergic neurons. Other pathologies such as lobar atrophies (Pick's disease, Creutzfeld-Jakob's disease), dementia with Lewy bodies, vascular dementias, Parkinson's disease, are associated with significant death of neurons at the origin of the symptoms of these dementias.

Presently, there is no effective treatment for checking neuronal degenerations. A therapeutic approach for protecting neurons from death is the supply of neurotrophic proteins.

These proteins, such as the BDNF (brain-derived neurotrophic factor), the CNTF (ciliary neurotrophic factor), the NGF (nerve growth factor), the GDNF (glia-derived neurotrophic factor) are synthesized during embryonic development or after lesion in adults. These growth factors promote survival, maturation and differentiation of neuronal cells. Further, they inhibit apoptotic mechanisms, activate multiple survival routes, and protect a large number of neuronal populations. Their use is proposed in most neuronal degenerations.

Compounds which would activate the expression of neurotrophic factors or which would mimic the action of these factors have therapeutic potential for treating neurodegenerative syndromes.

In particular, the provision of neurotrophic molecules for treating neuronal degenerations is directed at three goals:

compensate for a potential deficiency in neurotrophic factors related to a lack of supply by the peripheral or central targets of the neurons and/or a disorder of the retrograde transport of these factors;

intervene in a non-specific way, on the biochemical routes involved in the degenerative cascade;

promote the natural compensating phenomena of dendritic growth and arborization of the nerve endings.

These compounds would therefore have a beneficial effect in a large number of pathologies in particular in pathologies affecting the peripheral and central nervous system.

Moreover, within the scope above, motoneurons are neurons notably present in the spinal cord and brain stem. Their degeneration or their death may lead to gradual weakening of the muscles of the limbs, and then to atrophy and possibly to spasticity (i.e. permanent contraction) of the muscle.

The most important pathologies which result from the degeneration or death of spinal and/or bulbar motoneurons are amyotrophic lateral sclerosis, also known as Charcot's disease or even as Lou Gehrig's disease, and spinal amyotrophies, in particular infantile spinal amyotrophies, also known as Werdnig-Hoffmann's disease or Kugelberg-Welander's disease.

Further, degeneration of the motoneurons is observed in the case of traumas with crushing and/or sectioning of the spinal cord or the peripheral motor nerves.

More generally, the term of spinal amyotrophies is used for diseases where degeneration and death of the motoneurons of the spinal cord are involved.

Amyotrophic lateral sclerosis (ALS) is a neurodegenerative disease associated with different types of inclusions such as Lewis bodies and characterized by the degeneration of spinal and cortical motoneurons, the fatal outcome of which is sometimes associated with frontal dementia. During development of ALS, degenerative phenomena occur not only in the brain but also in the spinal cord and accordingly in the muscle, through lack of innervation.

Active compounds are still sought for controlling the aforementioned diseases. Now, the applicant has discovered that derivatives of cholest-4-en-3-one oxime and notably 3-oxyimino-cholest-4-en-6-one, were endowed with remarkable neuroprotective and/or cardioprotective properties.

Consequently, the attractive neuroprotective and cardioprotective properties of the compounds of formula I justify their use as a drug, particularly for preparing a cytoprotective drug, most particularly a neuroprotective or cardioprotective drug.

The term "cytoprotective" refers to the capacity of agents, e.g. chemical compounds, either natural or not, of maintaining interactions of the cells with each other or with the other tissues, of protecting the cells against degeneration phenomena leading to cell function loss or to undesirable cell activities, with or without cell death, and/or against cell dysfunctions and/or against degenerative diseases or affections leading to the cell dysfunctions, said dysfunctions or said diseases or affections either leading to cell death or not.

The terms "neuroprotective" or "cardioprotective" refer to the same properties of said agents but specifically for cells of the nervous system ("neuroprotective") or specifically for cells of the cardiac system ("cardioprotective").

It is therefore understood that a cytoprotective or neuroprotective or cadioprotective compound is a compound which has the properties as described earlier. This is why the object of the present invention is the use as drugs, of compounds fitting formula I

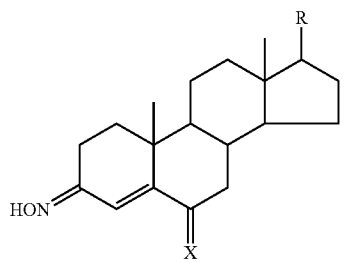

wherein

X represents an oxygen atom or a =N—OH group

R represents a group selected from

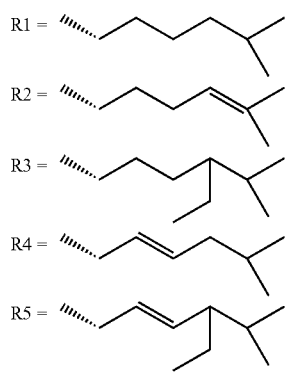

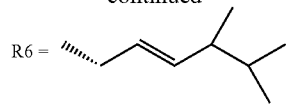

as well as their esters and/or addition salts with pharmaceutically acceptable acids.

Addition salts with pharmaceutically acceptable acids may for example be salts formed with hydrochloric, hydrobromic, nitric, sulphuric, phosphoric, acetic, formic, propionic, benzoic, maleic, fumaric, succinic, tartaric, citric, oxalic, glyoxylic, aspartic, alkane-sulfonic acids such as methane- or ethane-sulfonic acids, aryl-sulfonic acids, such as benzene- or paratoluene-sulfonic acids, or carboxylic acids.

Thus, the object of the invention is also the use as a drug of cholest-4-en-3,6-dioxime, cholest-4,22-dien-3,6-dioxime, cholest-4,24-dien-3,6-dioxime, 3-oxyimino-cholest-4-en-6-one, 3-oxyimino-cholest-4,22-dien-6-one, 3-oxyimino-cholest-4,24-dien-6-one, 24-methyl-3-oxyimino-cholest-4,22-dien-6-one, 24-methyl-cholest-4,22-dien-3,6-dioxime, 24-ethyl-cholest-4-en-3,6-dioxime, 24-ethyl-cholest-4,22-dien-3,6-dioxime, 24-ethyl-3-oxyimino-cholest-4-en-6-one, 24-ethyl-3-oxyimino-cholest-4,22-dien-6-one, as well as their esters, and/or their addition salts with pharmaceutically acceptable acids.

Among the compounds described above, the use of which is preferential as a drug, the compounds of formula I are notably retained for which X represents an oxygen atom, i.e. 3-oxyimino-cholest-4,24-dien-6-one, 3-oxyimino-cholest-4,22-dien-6-one, 3-oxyimino-cholest-4,24-dien-6-one, 24-methyl-3-oxyimino-cholest-4,22-dien-6-one, 24-ethyl-3-oxyimino-cholest-4-en-6-one, 24-ethyl-3-oxyimino-cholest-4,22-dien-6-one, as well as their esters and/or their addition salts with pharmaceutical acceptable acids.

More particularly 3-oxyimino-cholest-4-en-6-one and 24-ethyl-3-oxyimino-cholest-4-en-6-one are retained, as well as their esters and/or their addition salts with pharmaceutically acceptable acids.

Most particularly 3-oxyimino-cholest-4-en-6-one is retained as well as its esters and/or its addition salts with pharmaceutically acceptable acids.

The compounds, objects of the present invention, have very attractive pharmacological properties. They are notably endowed with remarkable cytoprotective properties, particularly neuroprotective properties, most particularly towards motoneurons, and cardioprotective properties.

These properties are illustrated in the experimental part hereafter. They justify the use of the compounds described above as well as that of their esters and/or their addition salts with pharmaceutically acceptable acids, and cytoprotective drugs, particularly as neuroprotective and/or cardioprotective drugs. Most particularly, the compounds according to the invention have remarkable activity towards motoneurons, neurons of the central nervous system, of the motor nerves and peripheral nerves.

Within the context of the invention, the term <<treatment>> designates preventive, curative, palliative treatment, as well as patient care (reducing suffering, improving lifetime, slowing down the progression of the disease), etc. The treatment may further be carried out in combination with other ingredients or treatments, such as notably other active compounds for treating the pathologies or traumas specified in the present application.

The compounds according to the present invention, owing to their cytoprotective properties, may be used for preparing a drug intended for treatment or prevention of necrosis and/or pathological apoptosis and/or necroptosis (anti-necrotic and/or anti-apoptotic and/or anti-necroptotic drugs) or even for the treatment or prevention of diseases such as:

- diseases of the bones, the joints, the connective tissue, and of cartilage, such as osteoporosis, osteomyelitis, arthritises including for example osteoarthritis, rheumatoid arthritis and psoriatic arthritis, avascular necrosis, progressive fibrodysplasia ossificans, rickets, Cushing's syndrome;
- muscular diseases such as muscular dystrophy, such as for example Duchenne's muscular dystrophy, myotonic dystrophies, myopathies and myasthenias;
- diseases of the skin, such as dermatitises, eczema, psoriasis, aging, or even alterations of scarring;
- cardiovascular diseases such as cardiac and/or vascular ischemia, myocardium infarction, ischemic cardiopathy, chronic or acute heart failure, cardiac dysrythmia, atrial fibrillation, ventricular fibrillation, paroxystic tachycardia, heart failure, anoxia, hypoxia, secondary effects due to therapies with anti-cancer agents;
- circulatory diseases such as atherosclerosis, arterial scleroses, peripheral vascular diseases, cerebrovascular strokes, aneurisms;
- haematological and vascular diseases, such as anemia, vascular amyloidosis, haemorrhages, drepanocytosis, red cell fragmentation syndrome, neutropenia, leukopenia, medullar aplasia, pancytopenia, thrombocytopenia, haemophilia;
- lung diseases including pneumonia, asthma; obstructive chronic diseases of the lungs such as for example chronic bronchitises and emphysema;
- diseases of the gastro-intestinal tract, such as ulcers;
- diseases of the liver including viral hepatitises and cirrhoses, diseases of the liver due to toxins or drugs;
- diseases of the pancreas such as for example acute and chronic pancreatitises;
- metabolic diseases such as diabetes mellitus and insipid diabetes, thyroiditises;
- diseases of the kidneys, such as for example acute renal disorders or glomerulonephritis;
- viral and bacterial infections such as septicaemia;
- severe intoxications by chemicals, toxins or drugs;
- degenerative diseases associated with the Acquired Immune Deficiency Syndrome (AIDS);
- disorders associated with aging such as the syndrome of accelerated aging;
- inflammatory diseases such as Crohn's disease, rheumatoid polyarthritis;
- auto-immune diseases such as erythematous lupus;
- dental disorders such as those resulting in degradation of tissues such as for example periodontitises;
- ophthalmic diseases or disorders including diabetic retinopathies, glaucoma, macular degenerations, retinal degeneration, retinitis pigmentosa, retinal holes or tears, retinal detachment, retinal ischemia, acute retinopathies associated with trauma, inflammatory degenerations, post-surgical complications, medicinal retinopathies, cataract;
- disorders of the audition tracts, such as otosclerosis and deafness induced by antibiotics;
- diseases associated with mitochrondria (mitochondrial pathologies), such as Friedrich's ataxia, congenital muscular dystrophy with structural mitochondrial abnormality, certain myopathies (MELAS syndrome, MERFF syndrome, Pearson's syndrome), MIDD (mitochondrial diabetes and deafness) syndrome, Wolfram's syndrome, dystonia.

Most particularly, the drugs according to the present invention find their use owing to their neuroprotective properties, for example in the treatment or prevention of neurodegenerative diseases, such as for example Huntington's disease, hereditary or sporadic neurodegenerative chronic diseases, neuronal lesions related to aging, peripheral, hereditary or lesional neuropathies, diabetic neuropathies or those induced by anti-cancer treatments, traumas of the brain, the peripheral nerves or the spinal cord, ischemias of the brain or of the spinal cord, epilepsies, hereditary, lesional or aging-related degenerations of sensorial neurons of vision or degenerations of the optical nerve, hereditary, traumatic or aging-related degenerations of the sensorial neurons of hearing, lobar atrophies and vascular dementias and notably spinal amyothrophies, amyotrophic lateral sclerosis and pathologies due to traumas of the spinal cord or of the peripheral motor nerves.

Notably owing to their neuroprotective properties towards motoneurons, they find their use particularly in the treatment of spinal amyotrophies, notably of amyotrophic lateral sclerosis or infantile spinal amyotrophies, and in the treatment of traumas of the spinal cord or of the peripheral motor nerves as mentioned above.

Generally, the daily dose of the compound will be the minimal dose for obtaining the therapeutic effect. This dose will depend on different factors as mentioned before. The dosages of the compound described above and for example, of 3-oxyimino-cholest-4-en-6-one will generally be comprised between 0.001 to 100 mg per kilogram daily for humans.

If required, the daily dose may be administered in two, three, four, five, six or more takings per day or with multiple subdoses administered at suitable intervals during the day.

The selected amount will depend on multiple factors, in particular on the administration route, on the administration time, on the moment of administration, on the elimination rate of the compound, on the different product(s) used in combination with the compound, on the age, on the weight and on the physical condition of the patient, as well as on his/her medical history and on any other information known in medicine.

The prescription of the attending physician may begin with dosages less than those generally used, and then these dosages will be gradually increased in order to better control the occurrence of possible secondary effects.

The object of the invention is also pharmaceutical compositions which contain at least one aforementioned compound or one of its esters and/or its addition salts with pharmaceutically acceptable acids, as an active ingredient.

In these compositions, the active ingredient is advantageously present at physiologically effective doses; the aforementioned compositions notably contain an effective neuroprotective dose of at least one active ingredient above.

As drugs, the compounds fitting formula I as well as their esters and/or their addition acids with pharmaceutically acceptable acids may be incorporated into pharmaceutical compositions intended for the digestive or parenteral route.

The pharmaceutical compositions according to the invention may further comprise at least one other therapeutically active ingredient, for simultaneous, separate use, or spread over time, notably upon treating a subject affected with a pathology or a trauma related to degeneration or death of cells, particularly of cardiac cells and/or motoneurons, as defined above.

The pharmaceutical compositions or drugs according to the invention advantageously comprise one or more inert, i.e. pharmaceutically inactive and non-toxic, excipients or carriers. For example saline, physiological, isotonic, buffer solutions, etc., may be mentioned, compatible with pharmaceutical use and known to one skilled in the art. The compositions may contain one or more agents or carriers selected from dispersants, solubilizers, stabilizers, preservatives, etc. Agents or carriers which may be used in the formulations (liquid and/or injectable and:or solid formulations) are notably methyl cellulose, hydroxymethyl cellulose, carboxymethyl cellulose, cyclodextrines, polysorbate 80, mannitol, gelatin, lactose, vegetal or animal oil, acacia, etc. The compositions may be formulated as an injectable suspension, as gels, oils, tablets, suppositories, powders, gelatine capsules, capsules, etc., possibly by means of galenic forms or of devices providing prolonged and/or delayed release. For this type of formulation, an agent such as cellulose, carbonates or starches are used advantageously.

Administration may be performed by any method known to one skilled in the art, preferably orally or by injection, typically via an intraperitoneal, intracerebral, intrathecal, intravenous, intra-arterial or intramuscular route. Oral administration is preferred. If this is a long term treatment, the preferred administration route will be sublingual, oral or transcutaneous.

For the injections, the compounds are generally packaged as liquid suspensions, which may be injected by means of syringes or perfusions, for example. It is understood that the flow rate and/or the injected dose or generally the dose to be administered, may be adapted by one skilled in the art depending oo the patient, on the pathology, on the administration method, etc. It is understood that repeated administrations may be performed, possibly in combination with other active ingredients or any pharmaceutically acceptable carrier (buffers, saline, isotonic solutions, in the presence of stabilizers, etc.).

The invention may be used in mammals, notably in humans.

The object of the present invention is further a method for preparing a composition as described above, characterized in that the active ingredient(s) are mixed, according to method known per se, with acceptable excipients, notably pharmaceutically acceptable excipients.

Some of the compounds of formula I as defined above are known or may be prepared according to methods described in the literature. But some of the derivatives of formula I are novel products.

This is why the object of the present application is also novel compounds fitting formula I

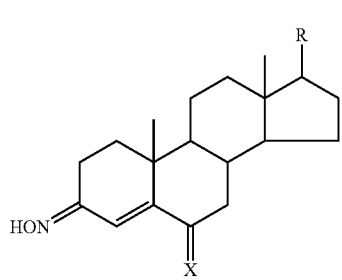

(I)

wherein X represents an oxygen atom or a =N—OH group and R represents a group selected from

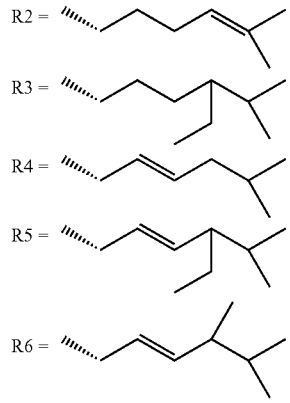

as well as their esters and/or their addition salts with mineral or organic acids.

Thus the object of the invention is a compound fitting the formula I above, selected from cholest-4,22-dien-3,6-dioxime, cholest-4,24-dien-3,6-dioxime, 3-oxyimino-cholest-4,22-dien-6-one, 3-oxyimino-cholest-4,24-dien-6-one, 24-methyl-3-oxyimino-cholest-4,22-dien-6-one, 24-ethyl-3-oxyimino-cholest-4,22-dien-6-one, 24-ethyl-3-oxyimino-cholest-4-en-6-one, 24-methyl-cholest-4,22-dien-3,6-dioxime, 24-ethyl-cholest-4-en-3,6-dioxime, as well as their esters and/or their addition salts with pharmaceutically acceptable acids.

Among the compounds described above, compounds of formula I are notably retained for which X represents an oxygen atom, as well as their esters and/or their addition salts with pharmaceutically acceptable acids, i.e. 3-oxyimino-cholest-4,22-dien-6-one, 3-oxyimino-cholest-4,24-dien-6-one, 24-methyl-3-oxyimino-cholest-4,22-dien-6-one, 24-ethyl-3-oxyimino-cholest-4-ene-6-one, 24-ethyl-3-oxyimino-cholest-4,22-dien-6-one, as well as their esters, and/or their addition salts with pharmaceutically acceptable acids.

More particularly 3-oxyimino-cholest-4,24-dien-6-one and 24-ethyl-3-oxyimino-cholest-4-en-6-one are retained, as well as their esters and/or their additional salts with pharmaceutically acceptable acids, and even more particularly 3-oxyimino-cholest-4,24-dien-6-one as well as its esters and its addition salts with pharmaceutically acceptable acids.

An object of the present invention is also a method for preparing novel compounds of formula I as defined above as well as their esters and/or their salts, characterized in that a compound of formula II is reacted

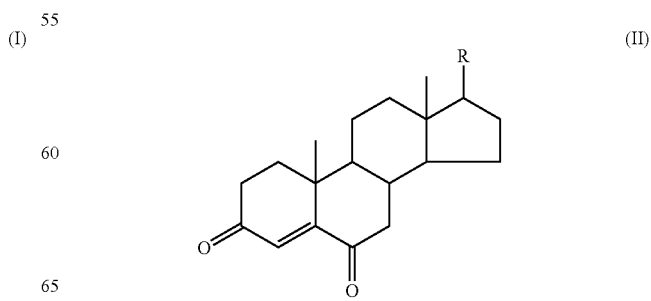

(II)

wherein
R represents a group selected from

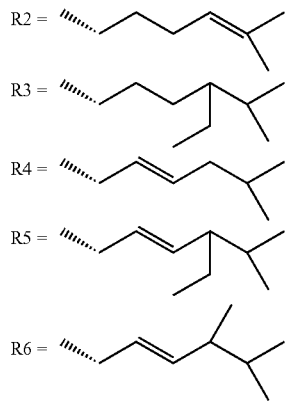

with a hydroxylamine halide such as hydroxylamine hydrochloride in order to obtain the expected compound of formula I which is isolated and salified if desired.

Under preferential conditions for applying the method as described above,
the starting product is solubilized in a minimum of suitable solvent such as for example pyridine,
either
 1 equivalent of hydroxylamine halide, in order to obtain in majority 3-oxyimino-6-one compounds; or
 an excess of hydroxylamine halide in order to obtain in majority 3,6-dioxime compounds is used;
this is performed under stirring for about 24 hrs at room temperature (20-30° C.).

The compounds of formula II are known derivatives, the synthesis of which is described in the literature.

The object of the invention is further the use of a compound of formula I

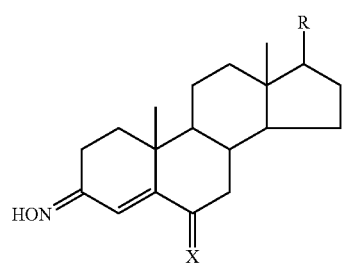

wherein X represents an oxygen atom or a =N—OH group, and R represents a group selected from

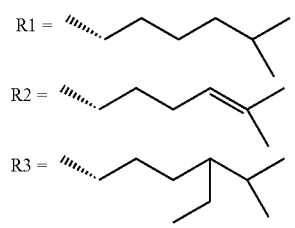

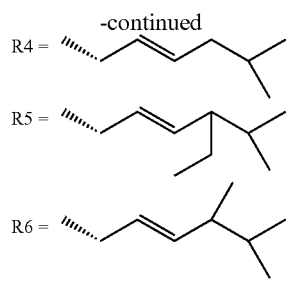

or one of its esters and/or its addition salts with pharmaceutically acceptable acids, for preparing a cytoprotective drug.

In particular, the object of the invention is the use of a compound of the above formula I in preparing a drug intended for the treatment or prevention of pathologies or traumas related to degeneration or death of cells, particularly of cardiac cells and/or neurons, whether the latter are natural or accidental.

More particularly, an object of the invention is further the use of a compound of the above formula I in preparing a drug intended for a treatment or for prevention of necrosis and/or pathological apoptosis and/or necroptosis (anti-necrotic and/or anti-apoptotic and/or anti-necroptotic drugs) or even for the treatment and prevention of diseases such as:

diseases of the bones, the joints, the connective tissue, and of cartilage, such as osteoporosis, osteromyelitis, arthritises including for example osteoarthritis, rheumatoid arthritis and psoriatic arthritis, avascular necrosis, progressive fibrodysplasia ossificans, rickets, Cushing's syndrome;

muscular diseases such as muscular dystrophy, such as for example Duchenne's muscular dystrophy, myotonic dystrophies, myopathies and myasthenias;

diseases of the skin, such as dermatitises, eczema, psoriasis, aging, or even alterations of scarring;

cardiovascular diseases such as cardiac and/or vascular ischemia, myocardium infarction, ischemic cardiopathy, chronic or acute heart failure, cardiac dysrythmia, atrial fibrillation, ventricular fibrillation, paroxystic tachycardia, heart failure, anoxia, hypoxia, secondary effects due to therapies with anti-cancer agents;

circulatory diseases such as atherosclerosis, arterial scleroses, peripheral vascular diseases, cerebrovascular strokes, aneurisms;

haematological and vascular diseases, such as anemia, vascular amyloidosis, haemorrhages, drepanocytosis, red cell fragmentation syndrome, neutropenia, leukopenia, medullar aplasia, pancytopenia, thrombocytopenia, haemophilia;

lung diseases including pneumonia, asthma; obstructive chronic diseases of the lungs such as for example chronic bronchitises and emphysema;

diseases of the gastro-intestinal tract, such as ulcers;

diseases of the liver including viral hepatitises and cirrhoses, diseases of the liver due to toxins or drugs;

diseases of the pancreas such as for example acute and chronic pancreatitises;

metabolic diseases such as diabetes mellitus and insipid diabetes, thyroiditises;

diseases of the kidneys, such as for example acute renal disorders or glomerulonephritis;

viral and bacterial infections such as septicaemia;

severe intoxications by chemicals, toxins or drugs;

degenerative diseases associated with the Acquired Immune Deficiency Syndrome (AIDS);

disorders associated with aging such as the syndrome of accelerated aging;

inflammatory diseases such as Crohn's disease, rheumatoid polyarthritis;

auto-immune diseases such as erythematous lupus;

dental disorders such as those resulting in degradation of tissues such as for example periodontitises;

ophthalmic diseases or disorders including diabetic retinopathies, glaucoma, macular degenerations, retinal degeneration, retinitis pigmentosa, retinal holes or tears, retinal detachment, retinal ischemia, acute retinopathies associated with trauma, inflammatory degenerations, post-surgical complications, medicinal retinopathies, cataract;

disorders of the audition tracts, such as otosclerosis and deafness induced by some antibiotics;

diseases associated with mitochrondria (mitochondrial pathologies), such as Friedrich's ataxia, congenital muscular dystrophy with structural mitochondrial abnormality, certain myopathies (MELAS syndrome, MERFF syndrome, Pearson's syndrome), MIDD syndrome (mitochondrial diabetes and deafness), Wolfram's syndrome, dystonia and particularly neurodegenerative diseases such as for example Huntington's disease, hereditary or sporadic neurodegenerative chronic diseases, neuronal lesions related to aging, hereditary or lesional peripheral neuropathies, Charcot-Marie-Tooth's disease, diabetic neuropathies or those induced by anticancer treatments, epilepsies, traumas of the brain, the peripheral nerves or the spinal cord, ischemias of the brain or the spinal cord, hereditary, lesional or aging-related degenerations of sensorial neurons of vision or degenerations of the optical nerve, hereditary, traumatic or aging-related degenerations of sensorial neurons of hearing, lobar atrophies and vascular dementias, diseases and traumas related to degeneration of motoneurons and more particularly particularly infantile spinal amyotrophies amyotrophic lateral sclerosis, multiple sclerosis and traumas of the spinal cord or of the peripheral motor nerves.

Most particularly the object of the invention is the use of a compound of formula I in the preparation of a drug intended for the treatment of particularly infantile, spinal amyotrophies, and amyotrophic lateral scleroses.

Application of these drugs usually comprises the administration to the patients, particularly to mammals, most particularly to human beings, of a therapeutically effective amount of a compound of formula I and notably of 3-oxyimino-cholest-4-en-6-one, in particular in order to increase survival of the cells, particularly of cardiac cells and/or neurons or for promoting axonal growth.

The object of the invention is just as well a method for treating the aforementioned diseases, notably neurodegenerative diseases, and notably a method for treating pathologies or traumas related to the degeneration or death of neurons, in mammals (generally patients) affected with such pathologies or traumas, comprising the administration to these mammals of a therapeutically effective amount of 3-oxyimino-cholest-4-en-6-one, in particular for increasing neuron survival or promoting axonal growth.

Further, an object of the invention is a method for treating one of the diseases described above and notably pathologies or traumas related to the degeneration or death of motoneurons in mammals (generally patients) affected with such pathologies or traumas, comprising the administration to these mammals of a therapeutically effective amount of a compound of formula I, in particular for increasing neuron survival. More specifically, the pathologies related to the degeneration or death of motoneurons are amyotrophic lateral sclerosis or infantile spinal amyotrophies.

The following examples illustrate the invention without limiting it.

EXAMPLE 1

A suspension is prepared fitting the formulation:

| | |
|---|---|
| 3-oxyimino-cholest-4-en-6-one | 20 mg per ml |
| Excipient: | oleic acid |
| Preservative: | methylparaben |

EXAMPLE 2

Soft gelatin capsules are prepared fitting the formulation:

| | |
|---|---|
| 3-oxyimino-cholest-4-en-6-one | 250 mg |
| Excipient: sufficient amount for terminating a 750 mg gelatin capsule | |

EXAMPLE 3

Preparation of 3-oxyimino-cholest-4-en-6-one (R=R1)

In a 250 mL flask, 2.8 g of cholest-4-en-3,6-dione (7.03 mmol) are solubilized in 90 mL of pyridine at 0° C., and then 489 mg (7.3 mmol) of hydroxylamine hydrochloride are added. The solution is stirred for 12 hours by letting the temperature gradually rise up to room temperature. A 1 M HCl solution is added and then diethyl ether in order to perform extraction. The organic phases are dried on $MgSO_4$. After filtration, diethyl ether is evaporated off under reduced pressure. Purification is performed by flash chromatography (25/75 diethyl ether/petroleum ether) on silica gel followed by washing of the obtained solid with diisopropyl ether. 3-oxyimino-cholest-4-en-6-one is obtained as a white solid (530 mg, 1.28 mmol, 18%). Rf=0.58 (70/30 (diethyl ether/petroleum ether)).

Analyses:

Liquid chromatography/Mass spectrometry (Electrospray®)

Conditions of high performance liquid chromatography:

Column: Thermo-Hypersil Hyperprep—RP C18 8 μm-150×4.6 mm

Gradient: water (+0.05% TFA)/acetonitrile (+0.05% TFA)

t=0 min: 80% acetonitrile, 20% $H_2O$ t=15 min: 95% acetonitrile, 5% $H_2O$ t=27 min: 95% acetonitrile, 5% $H_2O$ Retention time: 20.32 min (units in $100^{ths}$ of min)

Peak detected in mass spectrometry: $\{M+H\}^+=414$

EXAMPLES 4 TO 8

The following compounds are prepared according to a procedure identical with that used in Example 3.

| Example No. | Prepared compound | Starting compound |
|---|---|---|
| 4 (R = R2) | 3-oxyimino-cholest-4,24-dien-6-one | cholest-4,24-dien-3,6-dione |
| 5 (R = R3) | 24-ethyl-3-oxyimino-cholest-4-en-6-one | 24-ethyl-cholest-4-en-3,6-dione |
| 6 (R = R4) | 3-oxyimino-cholest-4,22-dien-6-one | cholest-4,22-dien-3,6-dione |
| 7 (R = R5) | 24-ethyl-3-oxyimino-cholest-4,22-dien-6-one | 24-ethyl-cholest-4,22-dien-3,6-dione |
| 8 (R = R6) | 24-methyl-3-oxyimino-cholest-4,22-dien-6-one | 24-methyl-cholest-4,22-dien-3,6-dione |

EXAMPLE 9

Preparation of cholest-4-en-3,6-dioxime (R=R1)

In a 250 mL flask, 2.8 g of cholest-4-en-3,6-dione (7.03 mmol) are solubilized in 90 mL of pyridine at 0° C. and then 1,467 mg (21.09 mmol) of hydroxylamine hydrochloride are added. The solution is stirred for 12 hours by letting the temperature gradually rise up to room temperature. A 1 M HCl solution is added, followed by diethyl ether in order to perform extraction. The organic phases are dried on $MgSO_4$. After filtration, diethyl ether is evaporated off under reduced pressure. Purification is performed by flash chromatography (40/60 diethyl ether/petroleum ether) on silica gel. The obtained solid (778 mg) is recrystallized from diisopropyl ether. Cholest-4-en-3,6-dioxime is obtained as a white solid (487 mg, 1.14 mmol, 16%). Rf=0.21(70/30 (diethyl ether/petroleum ether)).

Analyses:
Liquid chromatography/Mass spectrometry (Electrospray®)
Conditions of high performance liquid chromatography:
Column: Thermo-Hypersil Hyperprep—RP C18 8 μm-150×4.6 mm
Gradient: water (+0.05% TFA)/acetonitrile (+0,05% TFA)
t=0 min: 80% acetonitrile, 20% $H_2O$
t=15 min: 95% acetonitrile, 5% $H_2O$
t=27 min: 95% acetonitrile, 5% $H_2O$
Retention time: 15.71 min and 17.61 min (units in $100^{ths}$ of min)
Peak detected in mass spectrometry: $\{M+H\}^+=429$

EXAMPLES 10 TO 14

The following compounds are prepared according to a procedure identical with that used in Example 9

| Example No. | Prepared compound | Starting compound |
|---|---|---|
| 10 (R = R2) | cholest-4,24-dien-3,6-dioxime | cholest-4,24-dien-3,6-dione |
| 11 (R = R3) | 24-ethyl-cholest-4-en-3,6-dioxime | 24-ethyl-cholest-4-en-3,6-dione |
| 12 (R = R4) | cholest-4,22-dien-3,6-dioxime | cholest-4,22-dien-3,6-dione |
| 13 (R = R5) | 24-ethyl-cholest-4,22-dien-3,6-dioxime | 24-ethyl-cholest-4,22-dien-3,6-dione |
| 14 (R = R6) | 24-methyl-cholest-4,22-dien-3,6-dioxime | 24-methyl-cholest-4,22-dien-3,6-dione |

Pharmacological Study

The compounds were tested according to the following procedures:

EXAMPLE 15

Effects of the Compounds of Formula I on Survival of Motoneurons

In order to demonstrate the neuroprotective action of the compounds of formula I, the applicant investigated their activity in an in vitro trophic deprivation model of rat motoneurons. It may be helpful to refer to Patent Application WO 0142784 of the applicant on the culture of spinal cord motoneurons.

The spinal cord of E14 rat embryos is dissected and the ventral portion is dissociated by trituration after trypsinization. The motoneurons are separated from the other spinal cells by a known method (Camu et al, 1993, Purification of spinal motoneurons from chicken and rat embryos by immunopanning. In <<Immunoselection Strategies for Neural cell culture>>), Neuroprotocols: A companion to Methods in Neurosciences 2, 191-199; Henderson et al., 1993, Neutrophins promote motor neuron survival and are present in embryonic limb bud. Nature 363 (6426):266-70). The cells are centrifuged on a density gradient. The motoneurons are enriched with the fraction of large (the less dense) cells. The cells of this fraction are incubated with an anti-p75 antibody, a surface antigen present on motoneurons. Secondary antibodies coupled with magnetic beads are added and the cell mixture is passed through a column in a magnet (Arce et al, 1999 Cardiotrophin-1 requires LIFRbeta to promote survival of mouse motoneurons purified by a novel technique. J. Neurosci Res 55(1): 119-26). Only motoneurons are retained: their purity is of the order of 90%.

The motoneurons are sown at low density in culture wells on a polyornithine-laminine substrate in a neurobasal medium (GIBCO) supplemented according to Raoul et al, 1999, Programmed cell death of embryonic motoneurons triggered through the Fas death receptor. J. Cell. Biol. 147(5): 1049-62. Negative (absence of trophic factors) controls and positive controls (in the presence of 1 ng/ml BDNF (Brain-Derived Neurotrophic Factor), 1 ng/ml GDNF (Glial-Derived Neurotrophic Factor) and 10 ng/ml CNTF (Ciliary Neurotrophic Factor) as marketed by the US company PEPROTECH, Inc. and Sigma-Aldrich) are included in each series.

The compounds to be tested are added 60 minutes after sowing and the cultures are maintained at 37° C. under 5% $CO_2$ for 3 days.

The motoneurons tend to die spontaneously in the absence of neurotrophic factors (Pettmann and Henderson, 1998, Neuronal cell death. Neuron 20(4):633-47). After 3 days, survival is evaluated by a fluorescence measurement after incubation of the cells in the presence of calcein which becomes fluorescent in living cells.

After 3 days of culture at 37° C. under 5% $CO_2$ and in saturating humidity, up to 50% of the initially sown motoneurons survive in the medium supplemented with neurotrophic factors, whereas less than 15% of the motoneurons survive in a culture medium not added with neurotrophic factors.

The neuroprotective activity of the compounds to be tested was evaluated by their capacity of preventing the death of motoneurons when they are added to the Neurobasal medium (GIBCO) as compared with survival of the motoneurons in a medium added with neurotrophic factors.

The compounds of formula I according to the invention have shown neuroprotective activity at a concentration capable of providing a better survival rate of the motoneurons in the Neurobasal medium. This survival rate is expressed by the number of living cells after treatment with the compound to be tested as compared with survival induced by neurotrophic factors. This ratio therefore represents the survival percentage due to the tested compound as compared with the survival induced by neurotrophic factors. If the ratio is greater than 0, the effect of the compound is positive for the survival of motoneurons.

The obtained results are the following:

| Compound of Example | Concentration in μM | Ratio |
| --- | --- | --- |
| 3 | 3 | 0.60 |
| 7 | 1 | 0.46 |
| 9 | 0.6 | 0.25 |
| 10 | 1 | 0.25 |
| 13 | 1 | 0.34 |

By virtue of their trophic effect on spinal motoneurons, the compounds of formula I according to the invention are therefore shown to be useful as a drug, notably in the treatment of amyotrophies, in particular in the treatment of amyotrophic lateral sclerosis or infantile spinal amyotrohies and in the treatment of traumas of the spinal cord.

EXAMPLE 16

Effects of the Compounds of Formula I on the Protection of Striatal Neurons Against Death Induced by Overexpression of a Mutated Form of Huntingtin Primary cultures of striatal neurons are prepared and they are described in the literature (Primary striatal neuronal culture, Mao L. et al., Methods Mol. Med., 2003, 79:379-86). The cells are electroporated according to the procedure described by Raoul et al., (Motoneuron death triggered by a specific pathway downstream of Fas. potentiation by ALS-linked SOD1 mutations Neuron, 2002, 35:1067-83) before sowing with an expression vector or plasmid containing a promoter element followed by the DNA coding for a truncated form of huntingtin which comprises the first 480 amino acids and 68 CAGs (Saudou et al., Huntingtin acts in the nucleus to induce apoptosis but death does not correlate with the formation of intranuclear inclusions, Cell, 1998, 95:55-66). A second expression vector containing the DNA coding for the green fluorescent protein (GFP) is also electroporated and is used as a reporter gene. The DNA of the plasmid coding for the huntingtin was prepared by purifying with cesium chloride. The plasmid containing the GFP sequence was prepared on Qiagen columns. The integrity of the DNA sequences is checked by sequencing, transfection and Western blotting. The cells which survive electroporation are sown at a density of 4,000 cellules per well of 96-well plates. The culture is accomplished in neurobasal medium (GIBCO) supplemented with pyruvate and B-27 (Beckton Dickinson). The cells are maintained in culture for 7 days without changing the medium.

The treatments with the compounds to be tested are performed just after sowing at a final concentration of 1 μM in 0.5% dimethylsulfoxide (DMSO). Positive controls are made by adding BDNF at a final level of 5 ng/ml. The negative controls only receive 0.5% DMSO.

Cell death is evaluated after 7 days by counting the number of living cells expressing GFP.

The activity of the compounds to be tested was evaluated by their capacity of preventing death of striatal neurons cultivated in the neurobasal medium as compared with the survival of striatal neurons in a medium supplemented with BDNF (Brain-Derived Neurotrophic Factor).

The obtained results are the following:

| Compound of example | Concentrations in μM | Ratio |
| --- | --- | --- |
| 3 | 1 | 0.3 |
| 9 | 0.3 | 0.5 |

At the concentration of $10^6$ M, the compounds to be tested show a protective effect against cell death induced by mutated huntingtin, right up to 60% as compared with BDNF-treated cells.

By virtue of their neuroprotective effect, the compounds of formula I according to the invention are therefore found to be useful as drugs intended for the treatment or prevention of neurodegenerative affections, notably in the treatment of spinal amyotrophies, amyotrophic lateral sclerosis, in the treatment of traumas of the spinal cord and of the peripheral nerves and in the treatment of Huntington's disease.

EXAMPLE 17

Effects of the Compounds of Formula I on the Protection of Cortical Neurons

Cortical neurons were prepared from Sprague-Dawley rat embryos in the E18 pregnancy stage and cultivated in a 96-well plate at a density of 333 cells/mm$^2$ in Neurobasal medium (Invitrogen) supplemented with 2% B27 (Invitrogen) and 2% sodium pyruvate. With these culture conditions, it is possible to obtain very good cortical neuron purity in the cultures. After 6 days in culture, the death of cortical neurons was induced by adding 10 μM camptothecin dissolved in dimethyl sulfoxide (DMSO). At the same moment, the neurons were treated with different concentrations of the compound to be tested. The final DMSO concentration after treatment is 1%. After 16 hours of incubation with camptothecin, the survival of the neurons was evaluated by counting the surviving cells. To do this, the cells were incubated for 20 minutes in the presence of a vital dye, calcein-AM (Invitrogen) at 2 μg/ml. After labelling, each culture well was analyzed by means of an imaging station (Flash Cytometer, TROPHOS, FRANCE) provided with an image analysis software package TINA 4.5 (TROPHOS, France) allowing acquisition of digital images of the whole of the well (exposure time 40 ms). The cells, defined by pixel size criteria (min=10; max=40), were then counted by means of the Tina 4.5 software package (TROPHOS)

The obtained results are the following:

Camptothecin induces a reduction in cell viability. Incubation of the cells with the compounds to be tested increases cell survival in a dose-dependent way with an EC50 of the order of hundreds of nM.

|  | Control | Compound 3 | | | |
| --- | --- | --- | --- | --- | --- |
|  |  | 0 | 0.1 µM | 0.3 µM | 1 µM |
| Cell viability (%) | 100 ± 18.4 | 43.2 ± 17.4 | 63.3 ± 20.3 | 99.1 ± 15.7 | 112.2 ± 22.3 |

Mean ± standard deviation, n = 8 wells

The invention claimed is:

1. A method for treating multiple sclerosis, comprising administering to a patient in need thereof 3-oxyimino-cholest-4-en-6-one, or one of its esters and/or its addition salts with pharmaceutically acceptable acids.

* * * * *

UNITED STATES PATENT AND TRADEMARK OFFICE
CERTIFICATE OF CORRECTION

PATENT NO.       : 8,481,515 B2
APPLICATION NO. : 12/158640
DATED            : July 9, 2013
INVENTOR(S)      : Drouot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 983 days.

Signed and Sealed this

Eighth Day of September, 2015

Michelle K. Lee
*Director of the United States Patent and Trademark Office*